United States Patent
Carraher et al.

(10) Patent No.: US 11,697,078 B2
(45) Date of Patent: Jul. 11, 2023

(54) HYBRID EXTRACTION PROCESS FOR CANNABINOIDS AND RELATED METHODS

(71) Applicant: MEDPHARM IOWA LLC, Des Moines, IA (US)

(72) Inventors: Jack McCaslin Carraher, Nevada, IA (US); Zach Joseph Baker, West Des Moines, IA (US)

(73) Assignee: MEDPHARM IOWA LLC, Des Moines, IA (US)

( * ) Notice: Subject to any disclaimer, the term of this patent is extended or adjusted under 35 U.S.C. 154(b) by 55 days.

(21) Appl. No.: 17/484,718

(22) Filed: Sep. 24, 2021

(65) Prior Publication Data

US 2022/0111308 A1 Apr. 14, 2022

Related U.S. Application Data

(60) Provisional application No. 63/083,642, filed on Sep. 25, 2020.

(51) Int. Cl.
| | | |
|---|---|---|
| *C07D 493/00* | (2006.01) | |
| *B01D 11/04* | (2006.01) | |
| *B01D 5/00* | (2006.01) | |
| *B01D 9/02* | (2006.01) | |

(52) U.S. Cl.
CPC .......... *B01D 11/0403* (2013.01); *B01D 5/006* (2013.01); *B01D 9/02* (2013.01); *B01D 11/0488* (2013.01); *B01D 11/0492* (2013.01); *C07D 493/00* (2013.01)

(58) Field of Classification Search
CPC .. C07D 493/00; B01D 11/0403; B01D 5/006; B01D 9/02
See application file for complete search history.

(56) References Cited

U.S. PATENT DOCUMENTS

| | | |
|---|---|---|
| 9,709,913 B2 | 7/2017 | Sandler et al. |
| 9,765,000 B2 | 9/2017 | Nadal |
| 2015/0203434 A1 | 7/2015 | Flockhart et al. |
| 2018/0125777 A1 | 5/2018 | Lindsay |
| 2020/0246406 A1 | 8/2020 | Speier |

FOREIGN PATENT DOCUMENTS

| | | |
|---|---|---|
| CA | 3070594 A1 | 4/2020 |
| WO | 2004016277 A2 | 2/2004 |

OTHER PUBLICATIONS

International Searching Authority, "Search Report and Written Opinion," issued in connection with International Patent Application No. PCT/US2021/051990, dated Dec. 27, 2021, 8 pages.

*Primary Examiner* — Sikarl A Witherspoon
(74) *Attorney, Agent, or Firm* — Nyemaster Goode P.C.

(57) ABSTRACT

The present invention relates to methods for treating *cannabis* biomass in order to isolate tetrahydrocannabinolic acid (THCA). In another aspect, the present invention relates to a process that involves purification followed by extraction of *cannabis* biomass to isolate and improve yields of high-purity crystalline extracts.

16 Claims, 2 Drawing Sheets

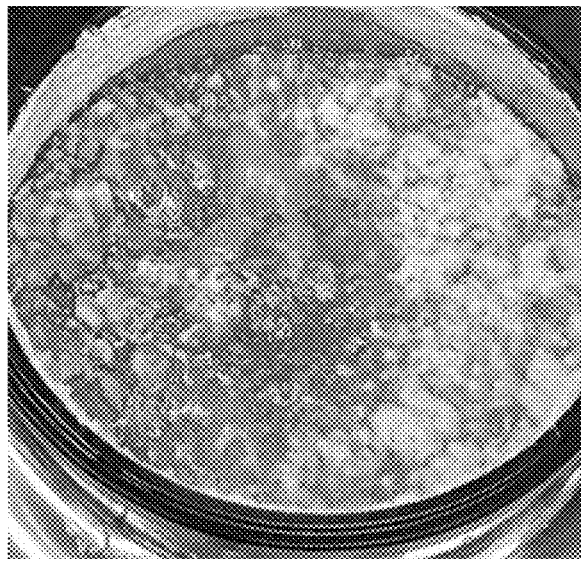 
FIG. 3A  FIG. 3B
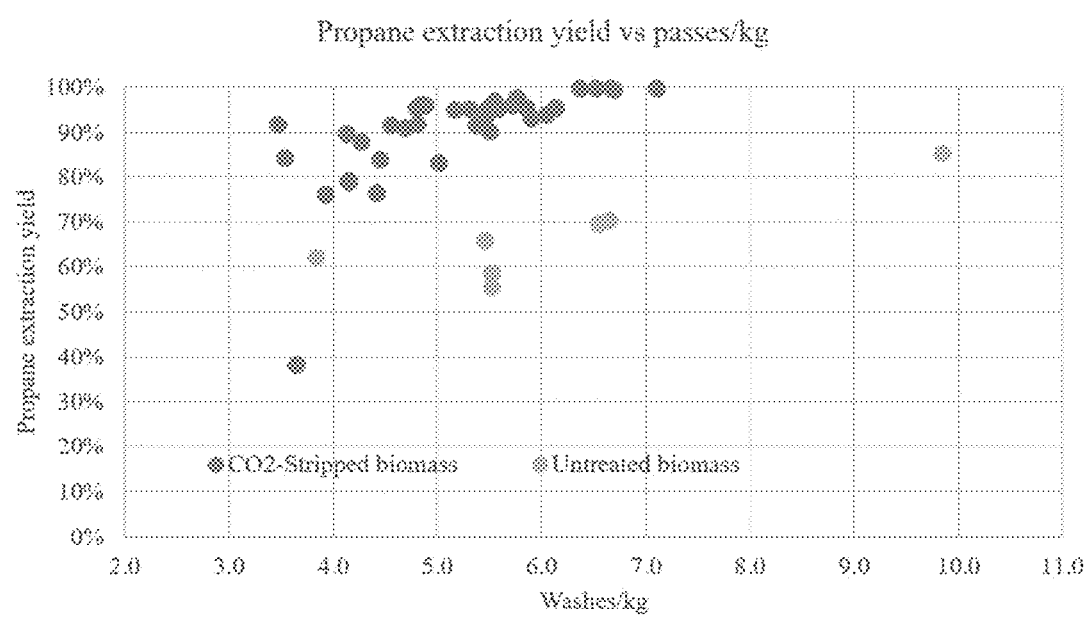
FIG. 4

HYBRID EXTRACTION PROCESS FOR CANNABINOIDS AND RELATED METHODS

CROSS-REFERENCE TO RELATED APPLICATIONS

This application claims the benefit of priority to U.S. Provisional Patent Application No. 63/083,642, filed Sep. 25, 2021, entitled "PIGGYBACK EXTRACTION PROCESS FOR CANNABINOIDS AND RELATED METHODS," the entire disclosure of which is hereby incorporated by reference in its entirety.

BACKGROUND OF THE INVENTION

Common methodologies for extraction of cannabinoids from *cannabis* materials utilize solvents (chiefly ethanol), liquid propane or butane, supercritical $CO_2$, or ice water with a series of sieves (bubble hash) methods. In order to obtain high concentration distillates (80-97%) from any of these methods, one must dewax at low temperature in ethanol or another organic solvent overnight, collect the organic solvent by rotary evaporation, and distill the dewaxed oil under vacuum at temperatures upward of 160° C. Achieving high purity (>90%) neutral cannabinoids often requires distillation multiple times. Yields from each iteration of distillation can range from about 30 to 70% due to degradation of cannabinoids at the high temperatures required for volatilization. Furthermore, the distillation process can take up to several days to obtain a single kilogram of purified distillate.

Alternatively, cannabinoid acid crystals can be formed by subjecting a saturated solvent to low temperature for long periods of time. However, to achieve the highest purities often up to 50% may be lost with each iteration in the process. The unrecovered cannabinoid acids can be recycled into the next batch and recovered in further iterations. Furthermore, distillation of cannabinoid acids is not feasible given decarboxylation of these acids occurs at temperatures well below their boiling point (even with vacuum applied to a pressure of 0.1 mbar). Decarboxylation can be observed at temperatures as low as 50° C. while vaporization of THC occurs at 160-170° C. at 0.1 mbar pressure with optimal equipment). Further still, some distillation equipment requires temperatures up to 260° C. due to poor vacuum and/or insulation on the column. The result is significantly lower yields and shorter shelf-stability once the distillate has cool to room temperature. Achieving such high temperatures resulted in poorer shelf-stability of some topical cream formulations ($t_{1/2}$=800±200 days vs 300±100 days for distillates achieving up to 185° C. vs 260° C., respectively) suggesting that a reactive and long-lived intermediate is formed at these higher temperatures and is still present when the distillate cools to room temperature and even when stored in the refrigerator. Accordingly, prior to the present invention, it has been virtually impossible to obtain THC without the requirement of achieving high temperatures during purification on an industrial scale.

Moreover, regulatory restrictions, such as limits or caps on the amount of $d^9$-tetrahydrocannabinol (THC) have required greater precision in the extraction process. For instance, attempts to extract tetrahydrocannabinolic acid (THCA) using well-known processes, such as using supercritical $CO_2$ followed by recrystallization to achieve high THCA yields, have been complicated by the relatively low extraction efficiency of the method for THCA. Prolonged extraction times under supercritical conditions yielded more THCA, but even under the harshest conditions only 24% efficiency was observed. The biomass remaining after $CO_2$ extraction ranged from 10-17 wt. % THCA. From an industrial standpoint, the resulting biomass is far too valuable to simply discard. Therefore, there has unmet and long-standing need to develop a process capable of increasing total yields of THCA from the biomass.

SUMMARY OF THE INVENTION

The present invention relates to methods for purification followed by extraction of *cannabis* biomass or what is referred herein as a "PiggyBack extraction" process. The process requires harvesting of *cannabis* plants, drying of biomass through either air-drying or by low temperature vacuum oven, destemming (optional, but recommended for efficiency), stripping terpenes and other cannabinoid or non-cannabinoid impurities with subcritical &/or supercritical $CO_2$, extraction of high purity cannabinoids/cannabinoid acids (up to 95% purity) with liquified hydrocarbon.

The crystalline cannabinoid acids contained may be used directly from the extractor, decarboxylated to yield neutral cannabinoids, esterified, oxidized, reduced, isomerized, or otherwise transformed either chemically, thermally or photochemically into alternative cannabinoids\cannabinoid acids of interest. Because the method described herein does not require decarboxylation to achieve high extraction yields (particularly necessary for supercritical $CO_2$ extraction) and decarboxylation can occur with purified crystalline extracts (i.e. after extraction), the space utilization in a vacuum oven can be increased dramatically (ca. 5-fold compared to biomass containing 20% cannabinoid acid; 10-fold with 10% cannabinoid acid biomass) thus enhancing throughput. Decarboxylation of the highly pure extract also has the advantage of better heat transfer than decarboxylation within the biomass. Additionally, because the rate of decarboxylation can be greatly affected by the presence of other chemical species within the biomass (through matrix effects) and these species are not present in the extracted cannabinoid acids, shorter times and lower temperatures are permissible for decarboxylation (i.e. higher yields can be obtained). The purity of the crystalline material obtained from the extract is sufficiently high that no further processing is necessary to obtain a usable distillate with greater than 95% purity. Thus, precipitation of fats, waxes and other phytochemical impurities followed by distillation is not required resulting in a significant cost savings due to lower initial capital expense, shorter operations time and avoidance of massive losses in yield due to one or multiple distillations or recrystallizations to achieve the desired purity. Throughput can be roughly doubled by removing the time-consuming step of distillation. Furthermore, the purification with subcritical and/or supercritical $CO_2$ yields a mixture of terpenes and neutral cannabinoids that can be processed by standard means and sold.

In at least one embodiment, the impurities can be stripped out using other solvents (such as, for instance, fluorinated hydrocarbons like tetrafluoroethylene or slightly acidic/neutral water) that are selective to dissolution of terpenes and/or neutral cannabinoids so long as dissolution of cannabinoid acids is limited. Alternatively, solvents that are capable of solubilizing cannabinoid acids, but have a slower rate of solubilization relative to solubilization of impurities may be employed with special emphasis being placed on the time component of the stripping extraction. The parameters for subcritical and/or supercritical $CO_2$ stripping of impurities can be adjusted as needed to obtain either high yields with high purities of neutral cannabinoids and cannabinoid acids or under harsher conditions over longer periods of time to strip neutral cannabinoids like CBG, CBD, or THC from the biomass yielding only high purity THCA upon secondary extraction.

The cannabinoids obtained in the stripping process can be recovered through standard precipitation→distillation methods. Liquified hydrocarbon extraction of the stripped biomass yields an extract with composition consistent with the pre-extraction (stripping) parameters. For instance, a subcritical $CO_2$ stripping primarily removes terpenes from the biomass while a combination of subcritical and supercritical $CO_2$ stripping also removes neutral cannabinoids. The former resulting extract from these scenarios contains a mixture of neutral cannabinoids with total purities (THC+THCA) of up to 91% and the latter yielding an extract containing primarily cannabinoid acids with average purities of 97% for THCA (the remaining constituents being primarily CBGA and THC). Decarboxylation of the 97% material on a 1-gram scale yielded THC measuring 100±1% purity by HPLC analysis.

DETAILED DESCRIPTION OF THE FIGURES

FIG. 3A is a photograph depicting the extract from propane extraction of dried *cannabis* biomass.

FIG. 3B is a photograph depicting the extract from propane extraction of $CO_2$-stripped *cannabis* biomass.

FIG. 4 depicts the propane extraction yield efficiency vs. passes of the present invention.

DETAILED DESCRIPTION OF THE INVENTION

Figure 1:
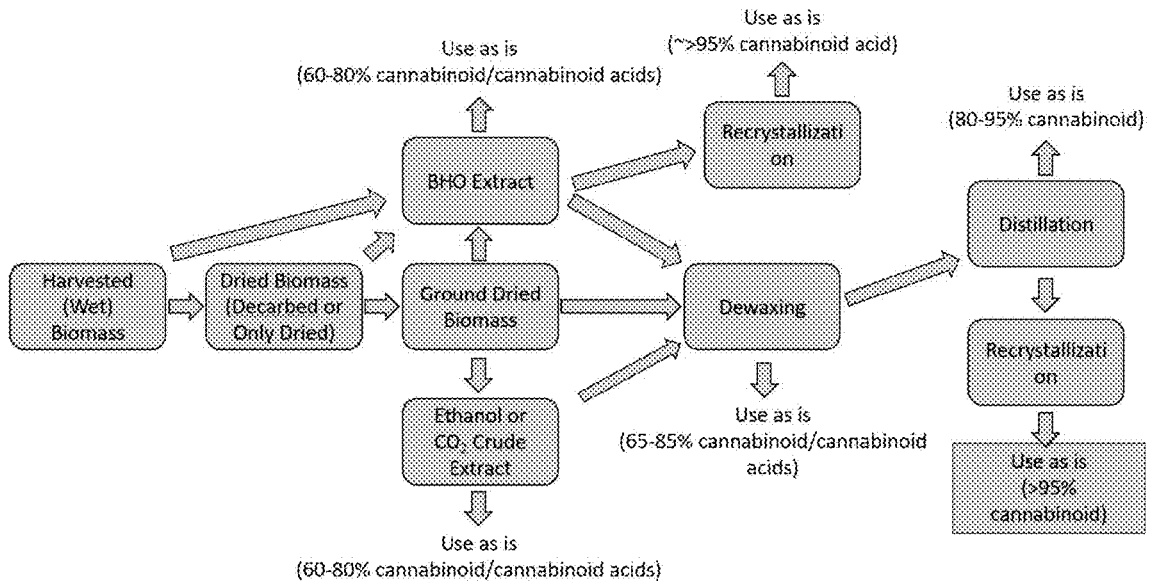
FIG. 1 depicts a process flow diagram of conventional processing methods.
Figure 2:
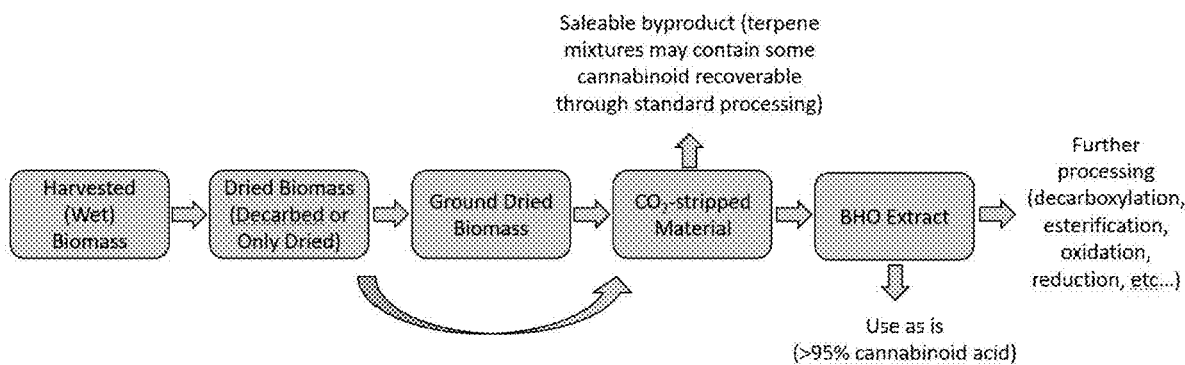
FIG. 2 depicts a process flow diagram of at least one embodiment of the present invention.

Standard industrial processing of *cannabis* biomass has conventionally required the following steps: 1) harvest 2) drying/curing 3) decarboxylation (in the case of $CO_2$ extraction, not required for cryogenic ethanol, liquified hydrocarbon extraction or bubble hash preparation). If a high purity distillate is required then the extract may optionally undergo 4) precipitation of fats and waxes and 5) distillation or recrystallization. Failure to dewax many extracts prior to distillation can result in a turbid distillate that is deemed aesthetically undesirable. Alternatively, some extracts are used as is to take advantage of a full terpene/cannabinoid profile. These processing steps and associated purities are shown in the process flow diagram, as depicted in FIG. 1. Yields are not shown but the entire process can easily be <65% after distillation and even lower if multiple distillations were required to achieve the desired purity. Alternatively, the method described herein requires 1) harvesting *cannabis* biomass 2) drying/curing 3) pre-extraction to strip the material of impurities 4) extraction of high purity cannabinoid acids. The material may be further processed through decarboxylation, esterification, oxidation, reduction, glycosylation, isomerization, or other transformations to achieve the desired final product. The process is shown in FIG. 2.

Liquified hydrocarbon extraction typically yields a mixture of cannabinoids, cannabinoid acids, terpenes, and other phytochemicals. PiggyBack extraction yields high purity crystalline extracts. Both extracts are shown in FIG. 3.

In at least one embodiment, $CO_2$-stripping of impurities from the biomass should occurred between pressures and temperatures that are consistent with $CO_2$ being in the subcritical or supercritical phase. For this work subcritical conditions were 1000-1100 psi and 55-75° F. for approximately 8-15 min/kg biomass, and supercritical conditions were 3000-5000 psi and 80-120° F. for approximately 37 min/kg biomass. However, any temperature and pressure in which $CO_2$ can be made a liquid or supercritical fluid will work provided the conditions are not so harsh as to degrade the target molecules. The extracts primarily contained terpenes (subcritical) or a combination of terpenes, fats, waxes, other impurities and cannabinoids (cannabidiolic acid, CBDA, and cannabigerolic acid, CBGA, were observed in these mixtures along with traces of THCA when extraction times were long enough).

In at least one embodiment, the $CO_2$-stripped biomass may either be removed and transferred to a liquified hydrocarbon extractor or the biomass containing vessel for used for $CO_2$ extraction may be attached to a liquified hydrocarbon vessel (input) and collection vessel (output). Dewaxing columns and recirculatory systems may be optionally employed, however are not required.

According to at least one embodiment, the liquified hydrocarbon extraction should occur by filling the biomass containing vessel with liquified propane or butane such that headspace is limited to roughly <5% of the extraction vessel. The liquified hydrocarbon may range in size from 1 carbon to 20 carbons. The hydrocarbon may be linear or branched, for instance butane and isobutane or octane and 2,2,4-trimethylpentane. Preferably, the liquified hydrocarbon will range from 2 to 8 carbons. Most preferably, hydrocarbons containing 3 to 5 carbon atoms are preferred due to their ability to solubilize cannabinoid acids and the ease with which they may be evaporated. Most preferably, the liquified hydrocarbon should be held at temperatures and pressures consistent with the hydrocarbon being in a condensed phase. For instance, according to one non-limiting example, temperatures on the order of about −5 to −25° C. (colder temperatures result typically resulted in lighter color extracts) and pressures on the order of about 100-150 psi should be maintained. The material should be allowed to steep until saturation is achieved (from about 1 to 10 minutes) before recovery of the liquified hydrocarbon wash is commenced. The biomass washes should continue until the desired mass of cannabinoid acid has been collected. Preferably this is known by HPLC analysis of the materials before hydrocarbon extraction. The system reaches saturation relatively quickly and the temperature as well as the cannabinoid acid to liquified hydrocarbon ratio determines the number of washes that must be achieved to ensure high yields. Collected cannabinoid acid was found to range in purity (THC+THCA) from 83-100%.

EXAMPLES

As mentioned above, regulatory restrictions, such as limits or caps on the amount of $d^9$-tetrahydrocannabinol (THC) have complicated the extraction process. For instance, attempts to extract tetrahydrocannabinolic acid (THCA) using well-known processes, such as using supercritical $CO_2$ followed by recrystallization to achieve high THCA yields were complicated by the relatively low extraction efficiency of the method for THCA. Prolonged extraction times under supercritical conditions yielded more THCA, but even under the harshest conditions only 24% efficiency was observed. These conditions also result in a higher fat content within the extract. The biomass remaining after $CO_2$ extraction ranged from 10-17 wt. % THCA. From an industrial standpoint, the resulting biomass is far too valuable to simply discard.

Recognizing this limitation, an attempt was made to perform a secondary extraction with ethanol. The extract was dark brown/green in colour and had purities on the order of 74% THCA. Purification with high pH water yielded material at 87% purity after the first bath, but the material was unstable when formulated and it is believed to be due to an unidentified impurity remaining from the process. The impurity catalysed decarboxylation even at room temperature when the material making it unsuitable for use in a THCA vaporization formulation that would meet the regulatory cap of no more than 3 wt. % THC (that did not at that time include THCA in the count). Redissolution in ethanol followed by slow vacuum assisted evaporation yielded white crystals, but care had to be taken to limit the amount of ethanol removed so that the liquid phase was still low enough in viscosity to filter without clogging. Attempts to wash the crystals, even with ice cold ethanol, resulted in more losses. An estimated 40% of the material was lost in the process.

Alternatively, hydrocarbon extraction is known to yield crude extracts from dried biomass with cannabinoid acid purities on the order of 65-80% with the bulk of the remaining mass being comprised of terpenes, some waxes, flavonoids and other phytochemicals. These extracts commonly look like slabs of thick oils with crystalline (undissolved) cannabinoid acid throughout. This in conjunction with solubility trends based on solvent functional groups previously observed by the researchers indicated that while hydrocarbons appear to be relatively good solvents for cannabinoid acids they are not nearly as efficient with neutral cannabinoids. It was, therefore, reasoned that a technique which strips the impurities from the biomass prior to the extraction of the cannabinoid acids should yield very high purity cannabinoid acids. The attempt to recover the cannabinoid acids remaining in the biomass from the $CO_2$ stripped biomass yielded crystalline material with purities typically ranging from 80-95% THCA (ca. 85-97% THC+ THCA). The THC in the final composition was dependent upon the amount of THC initially in the biomass and the $CO_2$ extraction parameters, where longer extraction time under supercritical conditions resulted in higher purity THCA from propane extraction due to the removal of THC from the biomass in the $CO_2$ extraction phase. Yields of THC & THCA from the stripped biomass were on the order of 90-95% provided a minimum of 5 washes/kg stripped biomass was performed, FIG. 4. Propane extraction of untreated biomass required up to 10 washes/kg to achieve similar efficiencies. It should be noted that any cannabinoids/cannabinoid acids extracted by the $CO_2$ can still be processed with standard techniques to recover them. Further, subcritical $CO_2$ extraction is known to be an effective method for harvesting terpenes which can also be sold directly or reintroduced into distillate containing products.

Further processing of the crystalline material through decarboxylation under vacuum (212° F. and −28 in Hg) indicated a stoichiometric conversion of THCA to THC and an HPLC chromatogram indicated a THC purity of 100.3% after only 3 hours. Not only has this method proved its utility for the production of cannabinoid acids, but it offers a route to the highest purity THC "distillate" on the market without requiring the time, expense or related losses in yield accumulated through extraction→dewaxing→distillation or recrystallization. In our own operation this has resulted in a time savings of approximately 56% and an enhancement in yield from 60% to 94% for the overall process. Alternative final processing of the extracted material may include esterification with an alcohol, oxidation or reduction, isomerization to $d^8$-THCA with acid catalysts or other transformations.

Harvested material was not decarboxylated as per usual protocol and was instead dried at 110° F. under −26 to −29 in Hg vacuum for 20 hours. Biomass was run through MPI's supercritical $CO_2$ extractor from Apex (see Table 1). Most runs consisted of a subcritical (900-1000 psi & 60-70° F.) extraction for 60-80 minutes followed by a supercritical extraction (2800-3000 psi & 110° F.) for 229-345 minutes. The yield of THCA from initial extraction ranged from 2.6-3.8 wt. % (16-24% extraction efficiency). The $CO_2$ extractions were done to remove terpenes and THC from the plant material in an effort to yield material with THCA and minimal THC. Methanol extraction and HPLC analysis on the 'spent' material revealed a range of 0.4-17.1 wt. %, however, it was discovered that there were significant inconsistencies in spent samples within a given run. Therefore, for the purposes of this disclosure the average difference (initial THCA-extracted THCA) was used for the initial conditions of the spent material. These values ranged from 10.8-13.4 wt. % (Ave(std dev)=12.3(0.9)%) relative the total mass of spent material.

TABLE 1

$CO_2$ pre-extraction conditions for dried (non-decarboxylated) material

| | $CO_2$ Phase 1 Conditions | | | | | $CO_2$ Phase 2 Conditions | | | | |
| --- | --- | --- | --- | --- | --- | --- | --- | --- | --- | --- |
| Expt | Time (min) | Pressure (psi) | Orifice Size | Chiller 1 Temp (° F.) | Chiller 2 Temp (° F.) | Time (min) | Pressure (psi) | Orifice Size | Chiller 1 Temp (° F.) | Chiller 2 Temp (° F.) |
| A | 60 | 910 | 37 | 60 | 90 | 301 | 2800 | 20 | 110 | 100 |
| B | 60 | 1000 | 37 | 70 | 90 | 60 | 3000 | 20 | 110 | 100 |
| C | 60 | 900 | 37 | 60 | 90 | 50 | 3000 | 20 | 110 | 100 |
| D | 60 | 950 | 37 | 65 | 90 | 45 | 3000 | 20 | 110 | 100 |
| E | 45 | 950 | 37 | 65 | 90 | 45 | 3000 | 20 | 110 | 100 |
| F | 60 | 950 | 37 | 65 | 90 | 76 | 3000 | 20 | 110 | 100 |
| G | 64 | 950 | 37 | 65 | 90 | 48 | 3000 | 20 | 110 | 100 |
| H | 63 | 950 | 37 | 65 | 90 | 47 | 3000 | 20 | 110 | 100 |
| I | 80 | 950 | 37 | 65 | 90 | 45 | 3000 | 20 | 110 | 100 |
| J | 65 | 3000 | 20 | 110 | 100 | 0 | Recovery | 37 | 110 | 100 |
| K | 90 | 1000 | 37 | 60 | 90 | 35 | 3600 | 20 | 110 | 100 |
| L | 90 | 950 | 37 | 65 | 90 | 41 | 3600 | 20 | 110 | 100 |
| M | 77 | 950 | 37 | 65 | 90 | 48 | 3600 | 20 | 110 | 100 |

TABLE 1-continued

CO₂ pre-extraction conditions for dried (non-decarboxylated) material

| | CO₂ Phase 1 Conditions | | | | | CO₂ Phase 2 Conditions | | | | |
|---|---|---|---|---|---|---|---|---|---|---|
| Expt | Time (min) | Pressure (psi) | Orifice Size | Chiller 1 Temp (° F.) | Chiller 2 Temp (° F.) | Time (min) | Pressure (psi) | Orifice Size | Chiller 1 Temp (° F.) | Chiller 2 Temp (° F.) |
| N | 69 | 950 | 37 | 65 | 90 | 46 | 3600 | 20 | 110 | 100 |
| O | 108 | 950 | 37 | 65 | 90 | 66 | 3600 | 20 | 110 | 100 |
| P | 51 | 950 | 37 | 65 | 90 | 39 | 3000 | 20 | 110 | 100 |
| Q | 45 | 100 | 37 | 70 | 90 | 59 | 3000 | 20 | 110 | 100 |
| R | 45 | 910 | 37 | 60 | 90 | 60 | 3000 | 20 | 110 | 100 |
| S | 60 | 900 | 37 | 60 | 90 | 38 | 3000 | 20 | 110 | 100 |
| T | 60 | 950 | 37 | 55 | 90 | 32 | 3000 | 20 | 110 | 100 |
| U | 45 | 1000 | 37 | 70 | 90 | 45 | 3000 | 20 | 110 | 100 |

Experiments A-R are with THCA forward biomass while S-U are with CBDA forward biomass

TABLE 2

Cannabinoid in biomass before CO₂ stripping and mass cannabinoid extracted

| Expt | Initial Biomass (kg) | Initial Cannabinoid | | Cannabinoid Acid | | Extracted Cannabinoid | | Cannabinoid Acid | |
|---|---|---|---|---|---|---|---|---|---|
| | | CBD (g) | THC (g) | CBDA (g) | THCA (g) | CBD (g) | THC (g) | CBDA (g) | THCA (g) |
| A | 4.070 | 0.0 | 12.2 | 0.0 | 735.0 | 0.0 | 28.5 | 1.1 | 153.3 |
| B | 4.500 | 0.0 | 28.9 | 1.8 | 710.7 | 0.0 | 25.1 | 0.9 | 46.6 |
| C | 4.500 | 0.0 | 28.9 | 1.8 | 710.7 | 0.0 | 25.1 | 0.9 | 46.6 |
| D | 4.250 | 0.0 | 301.4 | 0.3 | 383.9 | 0.5 | 97.4 | 0.3 | 31.3 |
| E | 4.250 | 0.0 | 301.4 | 0.3 | 383.9 | 0.5 | 97.4 | 0.3 | 31.3 |
| F | 3.855 | 0.0 | 273.3 | 0.3 | 348.2 | 0.0 | 77.0 | 0.8 | 57.0 |
| G | 4.500 | 0.0 | 60.0 | 1.5 | 696.2 | 0.0 | 51.0 | 0.5 | 37.2 |
| H | 4.250 | 0.0 | 69.4 | 0.8 | 676.4 | 0.1 | 61.8 | 0.6 | 40.8 |
| I | 4.250 | 0.0 | 69.4 | 0.8 | 676.4 | 0.1 | 61.8 | 0.6 | 40.8 |
| J | 4.360 | 0.0 | 71.2 | 0.8 | 693.9 | 0.0 | 51.8 | 0.4 | 59.6 |
| K | 4.500 | 0.0 | 33.5 | 1.2 | 796.9 | 0.2 | 27.0 | 0.9 | 50.9 |
| L | 4.500 | 0.0 | 33.5 | 1.2 | 796.9 | 0.2 | 27.0 | 0.9 | 50.9 |
| M | 3.500 | 0.0 | 41.2 | 1.0 | 653.6 | 0.1 | 31.2 | 0.6 | 40.7 |
| N | 3.130 | 0.0 | 36.9 | 0.9 | 584.5 | 0.1 | 27.9 | 0.5 | 36.4 |
| O | 4.335 | 0.0 | 32.3 | 1.1 | 767.7 | 0.0 | 27.9 | 0.9 | 60.9 |
| P | 3.615 | 0.0 | 33.5 | 1.6 | 683.5 | 0.2 | 18.2 | 0.7 | 32.3 |
| Q | 3.500 | 0.0 | 38.6 | 1.2 | 654.2 | 0.1 | 31.4 | 0.7 | 43.9 |
| R | 3.335 | 0.0 | 36.8 | 1.1 | 623.4 | 0.1 | 29.9 | 0.7 | 41.8 |
| S | 4.250 | 7.2 | 0.3 | 194.2 | 6.6 | 25.7 | 5.4 | 110.0 | 3.3 |
| T | 4.250 | 7.2 | 0.3 | 194.2 | 6.6 | 25.7 | 5.4 | 110.0 | 3.3 |
| U | 4.605 | 7.8 | 0.3 | 210.4 | 7.2 | 20.2 | 1.7 | 146.4 | 2.7 |

Experiments A-R are with THCA forward biomass while S-U are with CBDA forward biomass

TABLE 3

Liquid propane extraction conditions and yields

| Expt | Expt CO2 | Biomass (kg) | Mass Extract (kg) | THCA Purity | Total Cannabinoid Purity | Chiller (° C.) | Soak Time (min) | No. of Passes |
|---|---|---|---|---|---|---|---|---|
| 1 | P | 2.190 | 0.305 | 91.0% | 95.8% | −5--10 | 5 | 12 |
| 2 | A | 2.635 | 0.320 | 97.7% | 99.6% | −5 | 10 | 12 |
| 3 | A | 1.950 | 0.260 | 97.3% | 99.0% | −5 | 5 | 12 |
| 4 | B, C | 1.860 | 0.270 | 97.1% | 100.0% | −5--10 | 3 | 8 |
| 5 | B, C | 2.145 | 0.310 | 96.7% | 100.0% | −5--10 | 3 | 8 |
| 6 | B, C, F | 2.260 | 0.360 | 96.9% | 99.8% | −10 | 3 | 12 |
| 7 | B, C | 2.070 | 0.360 | 95.8% | 99.7% | −5--10 | 3 | 12 |
| 8 | B, C, D, E, F | 2.120 | 0.315 | 94.1% | 99.8% | −5--10 | 3 | 9 |
| 9 | D, E, F | 2.060 | 0.330 | 94.2% | 100.0% | −10 | 3 | 8 |
| 10 | D, E | 1.495 | 0.195 | 73.3% | 92.6% | −10 | 3 | 8 |
| 11 | D, E | 1.005 | 0.105 | 73.0% | 91.1% | −10 | 3 | 4 |
| 12 | D, E | 0.505 | 0.060 | 67.6% | 89.4% | −10 | 3 | 4 |

TABLE 3-continued

Liquid propane extraction conditions and yields

| Expt | CO2 | Biomass (kg) | Mass Extract (kg) | THCA Purity | Total Cannabinoid Purity | Chiller (° C.) | Soak Time (min) | No. of Passes |
|---|---|---|---|---|---|---|---|---|
| 13 | D, E, F | 2.315 | 0.300 | 69.7% | 96.2% | −10.5 | 3 | 8 |
| 14 | D, E | 2.065 | 0.270 | 71.6% | 93.6% | −10.5 | 2 | 8 |
| 15 | Q, R | 2.440 | 0.390 | 96.6% | 100.0% | −10.3 | 2 | 8 |
| 16 | Q, R | 2.490 | 0.400 | 96.7% | 100.0% | −10 | 1 | 12 |
| 17 | Q, R | 2.070 | 0.400 | 96.4% | 100.0% | −5 | 1 | 9 |
| 18 | H, I | 2.000 | 0.275 | 80.9% | 84.3% | −10 | 1 | 7 |
| 19 | G, H, I | 2.155 | 0.310 | 96.0% | 100.0% | −11.5 | 1 | 7 |
| 20 | G, H, I, J | 2.250 | 0.320 | 95.7% | 100.0% | −12 | 1 | 8 |
| 21 | H, I, J | 2.215 | 0.325 | 95.8% | 100.0% | −5 | 1 | 8 |
| 22 | S, T | 2.360 | 0.040 | 59.8% | 79.6% | −11.6 | 1 | 4 |
| 23 | S, T | 2.355 | 0.035 | 60.7% | 78.9% | −10 | 1 | 3 |
| 24 | S, T | 2.325 | 0.045 | 58.2% | 76.7% | −10 | 1 | 4 |
| 25 | G, H, I, J | 2.215 | 0.305 | 95.7% | 100.0% | −12.4 | 1 | 8 |
| 26 | G, H, I, J | 2.525 | 0.370 | 95.9% | 100.0% | −12.4 | 1 | 8 |
| 27 | G, H, I | 1.825 | 0.285 | 96.4% | 100.0% | −12.3 | 1 | 8 |
| 28 | G | 1.015 | 0.140 | 94.9% | 100.0% | −12.9 | 1 | 6 |
| 29 | O | 1.965 | 0.325 | 97.9% | 100.0% | −15 | 1 | 9 |

$CO_2$-stripped biomass was removed from the $CO_2$ extractor with a vacuum and collected in 5-gallon food grade buckets. The stripped material was loaded (typically at 2 kg) in a PX1 BHO extractor from Precision Extraction Solutions. A few experiments were done at lower and higher biomass loading. The only difference observed was that more biomass in the column requires more washes with liquified propane. The average yield of THCA for the propane extraction portion was 91±10% with an average purity of 92±9%. This represents 76±16% overall yield of THCA with from the biomass. The majority of the remaining cannabinoid in the biomass was extracted during $CO_2$ stripping.

Further experiments were conducted without drying in a vacuum oven (2 kg). This biomass was allowed to hang upside-down at room temperature (ca. 70° F.) for a minimum of 7 days with a dehumidifier running. This material was not ground and whole flower placed directly in the $CO_2$ extractor. Typical moisture content was typically <7% at the time of $CO_2$ pre-extraction. Experiments at >2 kg biomass required grinding to fit into the extractor (which in turn required vacuum oven drying). $CO_2$ pre-extraction conditions, cannabinoid masses, and propane extraction conditions and masses are shown in Tables 4-6.

TABLE 4

$CO_2$ pre-extraction conditions for air-dried (non-decarboxylated) material

| | | CO$_2$ Phase 1 | | | CO$_2$ Phase 2 | | |
|---|---|---|---|---|---|---|---|
| Expt | Mass (kg) | P (psi) | T (° F.) | Phase 1 Time min/kg | P (psi) | T (° F.) | Phase 2 Time min/kg |
| 1 | 2.000 | 950 | 65 | 16 | recovery | 65 | N/A |
| 2 | 2.000 | 950 | 65 | 16 | recovery | 65 | N/A |
| 3 | 2.000 | 950 | 65 | 16 | 3600 | 110 | 4 |
| 4 | 2.000 | 950 | 65 | 16 | 3600 | 110 | 12 |
| 5 | 4.000 | 950 | 65 | 16 | recovery | 65 | N/A |
| 6 | 2.000 | 950 | 65 | 18 | recovery | 65 | N/A |
| 7 | 4.000 | 950 | 65 | 18 | recovery | 65 | N/A |
| 8 | 4.250 | 950 | 65 | 18.8 | 3000 | 110 | 11 |
| 9 | 4.500 | 950 | 65 | 20 | 3600 | 110 | 9.1 |
| 10 | 4.500 | 1000 | 60 | 20 | 3600 | 110 | 7.8 |
| 11 | 3.500 | 950 | 65 | 22 | 3600 | 110 | 14 |
| 12 | 3.130 | 950 | 65 | 22 | 3600 | 110 | 15 |
| 13 | 1.980 | 950 | 65 | 23.2 | 3600 | 110 | 15 |
| 14 | 2.150 | 950 | 65 | 23.3 | 3600 | 110 | 15 |
| 15 | 2.105 | 950 | 65 | 23.3 | 3600 | 110 | 15 |
| 16 | 4.335 | 950 | 65 | 24.9 | 3600 | 110 | 15 |
| 17 | 2.000 | 950 | 65 | 25 | recovery | 65 | N/A |
| 18 | 2.000 | 950 | 65 | 30 | recovery | 65 | N/A |
| 19 | 2.000 | 950 | 65 | 25 | 3600 | 110 | 15 |
| 20 | 2.000 | 950 | 65 | 25 | 3600 | 110 | 15 |
| 21 | 2.000 | 950 | 65 | 25 | 3600 | 110 | 15 |
| 22 | 2.000 | 950 | 65 | 25 | Recovery | N/A | N/A |
| 23 | 3.890 | 950 | 65 | 12.9 | Recovery | N/A | N/A |

$CO_2$ pre-extraction conditions on air-dried THC/THCA forward biomass. Expts 5, 7-12, 16 & 23) were vacuum dried and ground to fit all biomass into the extractor.

TABLE 5

Cannabinoid in biomass before $CO_2$ stripping and mass cannabinoid $CO_2$-extracted

| Expt | initial mass | initial THC | initial THCA | Extracted THC | Extracted THCA |
|---|---|---|---|---|---|
| 1 | 2.000 | 20.0 | 342.0 | 2.7 | 5.0 |
| 2 | 2.000 | 50.4 | 329.0 | 9.0 | 3.7 |
| 3 | 2.000 | 21.6 | 251.4 | 9.0 | 7.3 |
| 4 | 2.000 | 50.4 | 329.0 | 20.8 | 31.5 |
| 5 | 4.000 | 84.0 | 740.0 | 16.7 | 8.0 |
| 6 | 2.000 | 20.0 | 360.0 | 4.7 | 10.2 |
| 7 | 4.000 | 84.0 | 740.0 | 19.0 | 10.5 |
| 8 | 4.250 | 68.0 | 675.8 | 59.8 | 39.0 |
| 9 | 4.500 | 31.5 | 796.5 | 19.4 | 37.0 |
| 10 | 4.500 | 31.5 | 796.5 | 22.9 | 40.2 |
| 11 | 3.500 | 42.0 | 654.5 | 34.0 | 42.5 |
| 12 | 3.130 | 37.6 | 585.3 | 21.6 | 34.7 |
| 13 | 1.980 | 49.9 | 325.7 | 24.3 | 22.7 |
| 14 | 2.150 | 54.2 | 353.7 | 28.0 | 21.7 |
| 15 | 2.105 | 53.0 | 346.3 | 17.0 | 14.1 |
| 16 | 4.335 | 30.3 | 767.3 | 27.9 | 60.9 |
| 17 | 2.000 | 56.0 | 392.0 | 22.3 | 11.9 |
| 18 | 2.000 | 54.0 | 382.0 | 20.2 | 10.2 |

TABLE 5-continued

Cannabinoid in biomass before $CO_2$ stripping and mass cannabinoid $CO_2$-extracted

| Expt | initial mass | initial THC | initial THCA | Extracted THC | Extracted THCA |
|---|---|---|---|---|---|
| 19 | 2.000 | 7.6 | 349.4 | 4.2 | 83.4 |
| 20 | 2.000 | 7.6 | 328.6 | 3.7 | 73.5 |
| 21 | 2.000 | 7.8 | 365.6 | 2.0 | 44.3 |
| 22 | 2.000 | 9.8 | 347.6 | 2.7 | 89.9 |
| 23 | 3.890 | 15.8 | 572.9 | 15.2 | 37.6 |

TABLE 3

Liquid propane extraction conditions and yields

| Expt | Mass In (kg) | Mass Propane Extract (g) | THC Purity % in Propane | THCA Purity % in Propane | THC + THCA purity % | Chiller temp (° C.) | Soak Time (min) | No. of passes |
|---|---|---|---|---|---|---|---|---|
| 1 | 1.975 | 302 | 3.5% | 86.9% | 90.4% | −8.4 | 1.0 | 9.5 |
| 2 | 1.910 | 380 | 8.4% | 81.1% | 89.5% | −15.7 | 1.0 | 11.0 |
| 3 | 1.910 | 295 | 2.9% | 83.1% | 86.0% | −21.6 | 1.0 | 11.0 |
| 4 | 1.795 | 285 | 7.5% | 79.1% | 86.6% | −24.1 | 1.0 | 11.0 |
| 5 | 3.875 | 655 | 4.8% | 81.1% | 85.9% | −9.4 | 1.0 | 20.0 |
| 6 | 1.820 | 238 | 3.5% | 87.1% | 90.6% | −7.7 | 1.0 | 7.5 |
| 7 | 3.890 | 690 | 4.3% | 82.7% | 87.0% | −6.8 | 1.0 | 19.0 |
| 8 | 3.950 | 516 | 3.5% | 89.2% | 92.7% | −10.4 | 1.0 | 13.9 |
| 9 | 4.183 | 753 | 2.3% | 95.1% | 97.4% | −12.0 | 1.0 | 18.5 |
| 10 | 4.183 | 753 | 2.3% | 95.1% | 97.4% | −12.0 | 1.0 | 18.5 |
| 11 | 3.228 | 552 | 2.9% | 94.0% | 96.9% | −12.0 | 1.0 | 12.7 |
| 12 | 2.887 | 493 | 2.9% | 94.0% | 96.9% | −12.0 | 1.0 | 11.3 |
| 13 | 2.000 | 310 | 6.1% | 85.2% | 91.3% | −19.8 | 1.0 | 11.0 |
| 14 | 2.020 | 290 | 4.9% | 85.7% | 90.6% | −18.3 | 1.0 | 11.0 |
| 15 | 2.015 | 320 | 5.7% | 85.3% | 91.0% | −19.3 | 1.0 | 11.0 |
| 16 | 3.955 | 700 | 3.2% | 96.5% | 99.7% | −13.7 | 1.0 | 18.0 |
| 17 | 1.865 | 330 | 7.0% | 83.4% | 90.4% | −16.3 | 1.0 | 11.0 |
| 18 | 1.880 | 335 | 7.7% | 83.4% | 91.1% | −15.4 | 1.0 | 11.0 |
| 19 | 1.690 | 250 | 1.1% | 90.1% | 91.2% | −25.0 | 1.0 | 12.0 |
| 20 | 1.795 | 260 | 1.1% | 90.1% | 91.2% | −25.0 | 1.0 | 12.0 |
| 21 | 1.800 | 275 | 1.1% | 89.0% | 90.1% | −25.0 | 1.0 | 12.0 |
| 22 | 1.840 | 305 | 1.2% | 89.1% | 90.3% | −25.0 | 1.0 | 12.0 |
| 23 | 3.770 | 315 | 1.1% | 86.5% | 87.6% | −25.0 | 1.0 | 12.0 |
| 24 | 1.375 | 225 | 1.8% | 75.0% | 76.9% | −5 to −10 | 5.0 | 9.0 |
| 25 | 1.355 | 225 | 1.8% | 74.9% | 76.7% | −5 to −10 | 3.0 | 9.0 |
| 26 | 1.650 | 250 | 1.8% | 76.8% | 78.6% | −5 to −10 | 10.0 | 9.0 |
| 27 | 1.630 | 225 | 1.9% | 75.1% | 77.0% | −5 to −10 | 10.0 | 9.0 |
| 28 | 1.565 | 225 | 2.1% | 76.2% | 78.2% | −5 to −10 | 10.0 | 6.0 |
| 29 | 1.630 | 215 | 2.1% | 74.3% | 76.4% | −5 to −10 | 5.0 | 9.0 |
| 30 | 0.915 | 175 | 2.1% | 78.6% | 80.6% | −5 to −10 | 3.0 | 9.0 |

Propane extraction results for air-dried $CO_2$-pre-extracted biomass (1-23) and for biomass with no $CO_2$ pre-extraction (24-30).

When only 2 kg of biomass was $CO_2$ pre-extracted the final purities (propane extract were higher). Colder propane extraction temperatures also typically resulted in a crystalline extract with less color.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

It should be further appreciated that minor dosage and formulation modifications of the composition and the ranges expressed herein may be made and still come within the scope and spirit of the present invention.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, and/or additions may be made, which are within the intended spirit and scope of the disclosure. From the foregoing, it can be seen that the exemplary aspects of the disclosure accomplishes at least all of the intended objectives.

The invention claimed is:

1. A method of extracting cannabinoids/cannabinoid acids from cannabis biomass comprising: drying cannabis biomass to form dried biomass; purifying the dried biomass by exposing the dried biomass to $CO_2$ to remove impurities and form a purified biomass; and extracting high purity cannabinoids/cannabinoid acids from the purified biomass with one or more liquified hydrocarbons selected from the group consisting of propane or butane, said extracting step occurring in a single vessel or closed system.

2. The method of claim 1 further including the step of decarboxylating the dried biomass.

3. The method of claim 2 whereby the decarboxylating step takes place either before or after the purifying step.

4. The method of claim 1 whereby the purifying step comprises contacting the dried biomass with subcritical $CO_2$ and/or supercritical $CO_2$.

5. The method of claim 1 that does not comprise a distilling step.

6. The method of claim 1 that does not comprise a decarboxylating step.

7. The method of claim 1 whereby the drying step comprises either air drying or use of a vacuum oven.

8. The method of claim 1 whereby the extracted cannabinoids/cannabinoid acids are at least 90% pure.

9. The method of claim 1 further including the step of destemming the cannabis biomass prior to the purifying step.

10. The method of claim 1 further including the step of precipitating fats and waxes from the purified biomass.

11. The method of claim 1 further including the step of grinding the dried biomass.

12. The method of claim 3 whereby the purification step is performed under subcritical conditions at a pressure of between about 1000-1100 psi and a temperature of between about 55-75° F.

13. The method of claim 3 whereby the purification step is performed under supercritical conditions at a pressure of between about 3000-5000 psi and a temperature of between about 80-120° F.

14. The method of claim 1 whereby the liquified hydrocarbon is in a condensed phase.

15. A method of extracting cannabinoids/cannabinoid acids from cannabis biomass comprising: drying cannabis biomass to form dried biomass; purifying the dried biomass by exposing the dried biomass to $CO_2$ to remove impurities and form a purified biomass; and extracting high purity cannabinoids/cannabinoid acids from the purified biomass with butane or propane, said method not including a distilling step.

16. The method of claim 1, wherein said extracting step occurs in the single vessel while maintaining a temperature of about −5 to −25° C.

\* \* \* \* \*